United States Patent [19]

Beach et al.

[11] 4,377,529

[45] Mar. 22, 1983

[54] SULFONATED GROUP VA YLIDES AND PROCESS FOR PREPARING SAME

[75] Inventors: David L. Beach, Gibsonia; Harrison, James J., Glenshaw, both of Pa.

[73] Assignee: Gulf Research & Development Company, Pittsburgh, Pa.

[21] Appl. No.: 209,674

[22] Filed: Nov. 24, 1980

Related U.S. Application Data

[63] Continuation-in-part of Ser. No. 179,079, Aug. 18, 1980, Pat. No. 4,293,502, and Ser. No. 179,078, Aug. 18, 1980, and Ser. No. 179,076, Aug. 18, 1980, Pat. No. 4,293,727, and Ser. No. 179,005, Aug. 18, 1980, Pat. No. 4,310,716.

[51] Int. Cl.³ .......................... C07F 9/70; C07F 9/72; C07F 9/90; C07F 9/50
[52] U.S. Cl. .................................. 260/440; 260/446; 568/9; 568/11; 568/13; 568/14; 568/15; 568/16; 564/282; 564/291
[58] Field of Search ................. 260/440, 446; 568/14, 568/15, 9, 11, 13, 16; 564/282, 291

[56] References Cited
U.S. PATENT DOCUMENTS
3,686,159  8/1972  Bauer et al. ........................ 260/94.9

OTHER PUBLICATIONS
Gilbert, "Sulfonation and Related Reactions", Interscience Publ., p. 61 (1965).
Nesmeyanov et al., "Sulfonation of Phosphorylides, Sulfobetaines", *Dok. Acad. Nauk SSSR*, vol. 151, No. 4, pp. 856–858 (1963).

Primary Examiner—Helen M. S. Sneed
Attorney, Agent, or Firm—Deane E. Keith; Forrest D. Stine; Joseph J. Carducci

[57] ABSTRACT

There are provided novel sulfonated group Va ylides defined by the following Formula I:

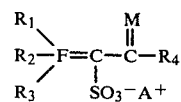

wherein $R_1$, $R_2$, $R_3$, and $R_4$ are either alike or different members selected from the group consisting of hydrogen, alkyl radicals having from about one to about 24 carbon atoms, preferably from about one to about 10 carbon atoms; aryl radicals having from about six to about 20 carbon atoms, preferably from about six to about 10 carbon atoms; alkenyl radicals having from about two to about 30 carbon atoms, preferably from about two to about 20 carbon atoms; cycloalkyl radicals having from about three to about 40 carbon atoms, preferably from about three to about 30 carbon atoms; aralkyl and alkaryl radicals having from about six to about 40 carbon atoms, preferably from about six to about 30 carbon atoms; a halogen radical selected from the group consisting of fluorine, chlorine, bromine and iodine, preferably chlorine; a hydroxyl group; an alkoxy or aryloxy group; a hydrocarbyl group, such as defined above, carrying halogen, hydroxyl, alkoxy or aryloxy; and a sulfonato group ($SO_3^-$) or an alkyl, aryl, alkenyl, cycloalkyl, aralkyl or alkaryl group carrying a sulfonato group; M is sulfur or oxygen, preferably oxygen; F is phosphorus, arsenic or antimony, preferably phosphorus; and A is the cationic residue of a base selected from the group consisting of an alkali metal hydroxide, an alkyl or aryl lithium, an alkoxide and a hydrocarbyl-substituted ammonium hydroxide.

The process for preparing these sulfonated ylides comprises sulfonating an ylide defined by the following Formula II:

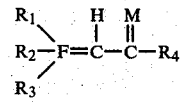

to obtain the sulfonated ylide defined by the following Formula III:

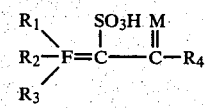

wherein $R_1$, $R_2$, $R_3$, $R_4$, F and M are as defined above. The sulfonated ylide is reacted with a base selected from the group consisting of an alkali metal hydroxide, an alkyl or aryl lithium, an alkoxide and a hydrocarbyl-substituted ammonium hydroxide to obtain the ylide defined by Formula I.

46 Claims, No Drawings

SULFONATED GROUP VA YLIDES AND PROCESS FOR PREPARING SAME

CROSS-REFERENCES TO RELATED APPLICATIONS

This application is a continuation-in-part of our U.S. patent application Ser. No. 179,079, filed Aug. 18, 1980, now U.S. Pat. No. 4,293,502 entitled "Nickel Ylides"; U.S. patent application Ser. No. 179,078, filed Aug. 18, 1980, entitled "Process for the Preparation of Nickel Ylides Containing Directly Sulfonated Ylide Ligands"; U.S. patent application Ser. No. 179,076, filed Aug. 18, 1980, U.S. Pat. No. 4,293,727 entitled "Process for the Oligomerization of Ethylene"; and U.S. patent application Ser. No. 179,005, filed Aug. 18, 1980, U.S. Pat. No. 4,310,716 entitled "Process for the Oligomerization of Ethylene in Methanol".

Reference is made to applicant's following U.S. applications:

U.S. patent application Ser. No. 210,413, filed Nov. 25, 1980, now U.S. Pat. No. 4,301,318 entitled "Process for Recovering Oligomerization Product".

U.S. patent application Ser. No. 209,673, filed Nov. 24, 1980, entitled "Novel Group VA Salts and Process for Preparing Same".

U.S. patent application Ser. No. 210,283, filed Nov. 25, 1980, entitled "Novel Group VA Ylides and Process for Preparing Same".

The disclosures of the foregoing applications are hereby incorporated by reference.

FIELD OF THE INVENTION

The present invention relates to novel sulfonated Group VA ylides which are useful in the preparation of nickel ylide catalysts for the oligomerization of ethylene. This invention also relates to a process for preparing such sulfonated ylides.

DESCRIPTION OF THE PRIOR ART

It is well known in the art to use a variety of catalysts to oligomerize ethylene to higher molecular weight olefins. The term "oligomerize" has been employed, and is employed herein to describe the conversion of lower olefins such as ethylene to olefinic products of higher molecular weight, e.g., to dimer, trimer, tetramer and the like. The reaction rate and product distribution obtained are highly dependent on the exact catalyst composition and the reaction conditions employed. Two such general classes of catalysts are the "Ziegler" types consisting of aluminum trialkyls and the "Ziegler-Natta" types consisting of aluminum alkyls or alkyl halides and titanium halides. Major disadvantages of aluminum alkyl catalysts are their highly reactive and pyrophoric nature and the fact that they must be used at relatively high temperatures, e.g., 200°–275° C. and pressures, e.g., 2000–4000 psig (13,790 to 27,580 kPa). Although much milder reaction conditions are used when the aluminum alkyls are used in conjunction with titanium halides, product quality and ease of catalyst separation from products of both of these prior art types of catalysts are not as high as desired.

An article by W. Keim, F. H. Kowaldt, R. Goddard and C. Kruger entitled "Novel Coordination of (Benzoylmethylene)triphenylphosphorane in a Nickel Oligomerization Catalyst", in *Agnew. Chem. Int. Ed. Engl.* (1978) No. 6, page 466, discloses the preparation of a nickel ylide by the following reaction:

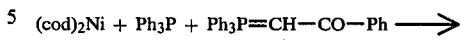

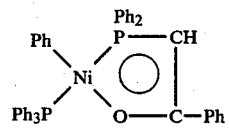

wherein "cod" represents 1,5-cyclooctadiene and "Ph" represents phenyl. It is reported that the resultant nickel ylide converts ethylene into alpha olefins or polyethylene.

SUMMARY OF THE INVENTION

The novel sulfonated Group VA ylides of this invention are defined by the following Formula I:

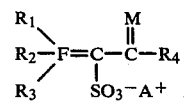

wherein $R_1$, $R_2$, $R_3$, and $R_4$ are either alike or different members selected from the group consisting of hydrogen, alkyl radicals having from about one to about 24 carbon atoms, preferably from about one to about 10 carbon atoms; aryl radicals having from about six to about 20 carbon atoms, preferably from about six to about 10 carbon atoms; alkenyl radicals having from about two to about 30 carbons atoms, preferably from about two to about 20 carbon atoms; cycloalkyl radicals having from about three to about 40 carbon atoms, preferably from about three to about 30 carbon atoms; aralkyl and alkaryl radicals having from about six to about 40 carbon atoms, preferably from about six to about 30 carbon atoms; a halogen radical selected from the group consisting of fluorine, chlorine, bromine and iodine, preferably chlorine; a hydroxyl group; an alkoxy or aryloxy group; a hydrocarbyl group, such as defined above, carrying halogen, hydroxyl alkoxy or aryloxy; and a sulfonato group ($-SO_3^-$) or an alkyl, aryl, alkenyl, cycloalkyl, aralkyl or alkaryl group carrying a sulfonato group; M is sulfur or oxygen, preferably oxygen; F is phosphorus, arsenic or antimony, preferably phosphorus; and A is the cationic residue of a base selected from the group consisting of an alkali metal hydroxide, an alkyl or aryl lithium, an alkoxide and a hydrocarbyl-substituted ammonium hydroxide.

The process for preparing the novel sulfonated ylides of this invention comprises sulfonating an ylide defined by the following Formula II:

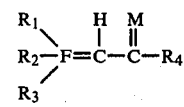

to obtain the sulfonated ylide defined by the following Formula III:

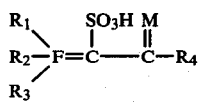

wherein R₁, R₂, R₃, R₄, F and M are as defined above. The sulfonated ylide is reacted with a base selected from the group consisting of an alkali metal hydroxide, an alkyl or aryl lithium, an alkoxide and a hydrocarbyl-substituted ammonium hydroxide to obtain the metal ylide defined by Formula I.

DESCRIPTION OF THE PREFERRED EMBODIMENTS

In the preparation of the sulfonated ylides of this invention, the first step involves sulfonating a ylide defined by the following Formula II:

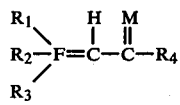

wherein each of $R_1$, $R_2$, $R_3$, $R_4$, F and M is as defined above to obtain the following sulfonated ylide defined by the following Formula III.

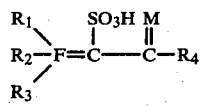

wherein each of $R_1$, $R_2$, $R_3$, $R_4$, F and M is as defined above. In some cases, for example, where $R_1$, $R_2$, $R_3$ and $R_4$ are phenyl, M is oxygen and F is phosphorous, the following Formula IIIa may more accurately described the structure:

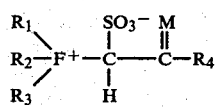

This first step can be done, for example, by dissolving the ylide of Formula II in a suitable solvent, for example, a halogenated hydrocarbon, such as chloroform, dichloroethane, methylene chloride or methyl chloroform, or a hydrocarbon solvent, such as heptane or hexane and then adding SO₃ to the resulting solution. The ylide and sulfonating agent are generally employed in equal molar amounts, although excess sulfonating agent can be present, if desired. Temperatures can be in the range of about 0° to about 200° C., preferably from about 20° to about 100° C., pressures can be elevated, although atmospheric pressure is preferred, and reaction times can vary from about five minutes to about 24 hours, preferably from about ten minutes to about four hours.

At the end of the reaction time the compounds defined by Formula III or IIIa are recovered by any suitable means. If the sulfonated desired product is solid, recovery can be effected by filtration, decantation or by centrifuging. If the desired product is dissolved in the reaction medium, recovery can be effected by distillation to remove the solvent therefrom.

The sulfonated product is converted to the corresponding ylide by reacting the same with a base, such as an alkali metal hydroxide (sodium or potassium hydroxide), an alkyl or aryl lithium (n-butyl lithium, methyl lithium or phenyl lithium), an alkoxide (sodium methoxide or potassium t-butoxide), a hydrocarbyl-substituted ammonium hydroxide (benzyltrimethylammonium hydroxide), etc., to produce the novel ylide defined by Formula I. This can be done, for example, by suspending or dissolving the sulfonated ylide in a suitable liquid, such as water, an alcohol (ethanol or isopropanol), an aromatic (benzene or toluene), a hydrocarbon (hexane or heptane), etc. The reaction temperature can range from about room temperature to about 200° C., preferably from about room temperature to about 50° C., and the reaction time from about one minute to about four hours, or even longer, but preferably from about one to about two hours. Elevated pressures can be used, although atmospheric pressure will suffice. If the ylide obtained is a solid, recovery can be effected by filtration, decantation or by centrifuging. If the ylide is dissolved in the solvent, simple distillation is sufficient to remove the solvent, leaving behind the solid ylide.

Specific examples of sulfonated ylides defined by Formula I which can be prepared in accordance with this invention are set forth in Table I. In this table and as used elsewhere herein, "Ph" represents phenyl, "Me" represents methyl, and "Et" represents ethyl.

TABLE I

| Compound | $R_1$ | $R_2$ | $R_3$ | $R_4$ | F | M | A |
|---|---|---|---|---|---|---|---|
| 1 | Ph | Ph | Ph | Ph | P | O | Na |
| 2 | Ph | Ph | Ph | Ph | P | O | K |
| 3 | Ph | Ph | Ph | Ph | P | O | Li |
| 4 | Ph | Ph | Ph | Ph | P | S | Na |
| 5 | Ph | Ph | Ph | Ph | P | O | NMe₄ |
| 6 | Ph | Ph | Ph | H | P | O | NMe₃CH₂Ph |
| 7 | Ph | Ph | Ph | CH₃ | P | O | Na |
| 8 | Ph | Ph | Ph | Ph—Ph | P | O | K |
| 9 | Ph | Ph | Ph | Ph | P | O | Li |
| 10 | Ph | Ph | Ph | Ph | P | O | NEt₄ |
| 11 | Ph | Ph | Ph | Ph | P | O | NMe₃Et |
| 12 | H | H | H | Ph | P | O | Na |
| 13 | Ph | Ph | Ph | Ph | As | O | K |
| 14 | Ph | Ph | Ph | OEt | P | O | Li |
| 15 | CH₃ | CH₃ | CH₃ | OCH₃ | As | O | NEt₃CH₂Ph |
| 16 | Ph |  | Ph |  | P | O | Na |

TABLE I-continued

| Compound | R₁  | R₂  | R₃  | R₄                  | F  | M | A     |
|----------|-----|-----|-----|---------------------|----|---|-------|
| 17       | Ph  | Ph  | Ph  | CH₃                 | P  | O | K     |
| 18       | CH₃ | CH₃ | CH₃ | OC₄H₉               | P  | O | Li    |
| 19       | Ph  | CH₃ | CH₃ | CH₃                 | As | S | NH₃Me |
| 20       | CH₃ | Et  | Ph  | —⟨O⟩—OCH₃           | P  | S | NH₃Ph |
| 21       | H   | Ph  | Ph  | H                   | P  | O | Na    |
| 22       | Ph  | Et  | Et  | CH₃                 | As | S | K     |
| 23       | Ph  | H   | H   | H                   | P  | O | Li    |
| 24       | Ph  | Ph  | Ph  | Ph                  | As | O | NMe₄  |

The novel ylides of this invention are useful in the preparation of nickel ylide catalysts defined by the following Formula IV:

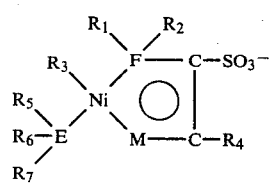

wherein $R_1$, $R_2$, $R_3$, $R_4$, F and M are as defined above; $R_5$, $R_6$ and $R_7$ can be the same as previously defined for $R_1$, $R_2$ and $R_3$; and E is phosphorous, arsenic, antimony or nitrogen, preferably phosphorous. To prepare the nickel ylide catalyst defined by Formula IV, the sulfonated ylide defined by Formula I is reacted with (1) a ligand defined by the formula:

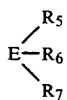

wherein $R_5$, $R_6$, $R_7$ and E are as defined above, and (2) a zero valent nickel compound, or any nickel compound convertible to a zero valent nickel compound in situ. Specific examples of ligands that can be used include: allyldiphenylphosphine; benzyldiphenylphosphine; bis(3-aminopropyl)phenylphosphine; bis(2-cyanoethyl)phenylphosphine; bis(m-fluorophenyl)phosphinous chloride; 4-bromophenyldiphenylphosphine; n-butyldiphenylphosphine; t-butyldiphenylphosphine; 2-cyanoethyldiphenylphosophine; cyclohexyldiphenylphosphine; n-decylphenylphosphine; diallylphenylphosphine; di-n-amylphenylphosphine; di-sec-butylphenylphosphine; dicyclohexylphenylphosphine; diethylphenylphosphine; di-n-heptylphenylphosphine; di-n-hexylphenylphosphine; dimethylphenylphosphine; di-methyl-p-tolylphosphine; diphenyl-n-butoxyphosphine; diphenylchlorophosphine; diphenylenephenylphosphine; diphenylethoxyphosphine; diphenylmethoxyphosphine; diphenylphosphine; beta-diphenylphosphinoethyltriethoxysilane; di-isopropylphenylphosphine; di-o-tolylphenylphosphine; divinylphenylphosphine; ethyldiphenylphosphine; n-hexyldiphenylphosphine; o-methoxyphenyldiphenylphosphine; (2-methylbutyl)diphenylphosphine; methyldiphenylphosphine; methylethylphenylphosphine; methylphenylphosphine; neomenthyldiphenylphosphine; pentafluorophenyldiphenylphosphine; (2-phenylbutyl)diphenylphosphine; phenyl-di-n-butoxyphosphine; phenyldichlorophosophine; phenyldimethoxyphosphine; phenylphosphine; isopropyldiphenylphosphine; n-propyldiphenylphosphine; o-tolyldiphenylphosphine; p-tolyldiphenylphosphine; tribenzylphosphine; tris(m-chlorophenyl)phosphine; tris(p-chlorophenyl)phosphine; tri(1-naphthyl)phosphine; triphenylphosphine; tris(4-dimethylaminophenyl)phosphine; tris(p-fluorophenyl)phosphine; tris(o-methoxyphenyl)phosphine; tris(p-methoxyphenyl)phosphine; tri-o-tolylphosphine; tri-m-tolylphosphine; tri-p-tolylphosphine; vinyldiphenylphosphine; sodium diphenylphosphinebenzene-3-sulfonate; disodium phenylphosphine-bis(benzene-3-sulfonate); dimethylphenylarsine; methyldiphenylarsine; triphenylarsine; tri-p-tolylarsine; diphenylchloroarsine; triphenylantimony; triphenylamine; tribenzylamine; methyldiphenylamine; dimethylphenylamine; bis(2-cyanoethyl)phosphine; bis(dimethylamino)methylphosphine; t-butyldichlorophosphine; 2-cyanoethylphosphine; cyclohexylphosphine; di-t-butylchlorophosphine; dicyclohexylphosphine; diethylethoxyphosphine; diethyl-iso-propoxyphosphine; diethylphosphine; triallylphosphine; tri-iso-butylphosphine; tri-n-butylphosphine; tri-sec-butylphosphine; tri-t-butylphosphine; triethylphosphine; tri-n-hexylphosphine; trimethylphosphine; trifluorophosphine; tri-iso-propylphosphine; tri-n-propylphosphine; tris(2-cyanoethyl)phosphine; tris(di-methylamino)phosphine; tris(trimethylsilyl)phosphine; tri-n-butylantimony; triethylarsine; trimethylarsine; methyldiiodoarsine; trimethylamine; triethylamine; tributylamine; tripropylamine; dimethylamine; di-n-hexylamine; dicyclohexylamine; diethylamine; tricyclohexylamine; ammonia; and phosphine. Specific examples of nickel compounds which can be used include: tris(triphenylphosphine)nickel; bis(cyclooctadiene)nickel; tetrakis(triphenylphosphine)nickel; bis(norbornadiene)nickel; (cyclooctta-1,5-diene)duroquinone nickel; (dicyclopentadiene)duroquinone nickel; bis(tetracyclone)nickel; tetrakis(triethylphosphine)nickel; tris(triethylphosphine)nickel; bis(triphenylphosphine)nickel dicarbonyl; nickel carbonyl; nickel(II)acetylacetonate; nickelocene; bis(triethylphosphine)nickel(II)chloride; tetrakis(trifluorophosphine)nickel; nickel acetate; nickel bromide; nickel carbonate; nickel chloride; nickel fluoride; nickel iodide; nickel nitrate; nickel sulfate; nickel 2,4-pentanedionate; bis π-allyl nickel; and nickel dichloride hexaamine.

Approximately equal molar amounts of each of the three reactants defined above are dissolved in any suitable unreactive solvent, such as toluene, tetrahydrofuran, dioxane, or other unreactive hydrocarbon solvents, and stirred while maintaining a temperature of about 0° to about 100° C., preferably room temperature, for about one-half hour to about 48 hours, preferably about three to about 20 hours, sufficient to ensure complete reaction. Any suitable pressure can be used, although atmospheric pressure is preferred. The solvent can be removed from the reaction mixture in any suitable manner, for example, by distillation, including vacuum distillation, if necessary, leaving behind the novel compound defined above. On the other hand, a second solvent in which the desired product is insoluble, such as heptane, can be added to the reaction product to precipitate the novel compound therein. The novel compound can be recovered, for example, by filtration, decantation or by centrifuging.

The following examples illustrate the invention, and are not intended to limit the invention, but rather, are presented for purposes of illustration. Example I illustrates the preparation of a sulfonated ylide of this invention; Example II illustrates the use of this sulfonated ylide in the preparation of a nickel ylide; and Examples III and IV illustrate the use of this nickel ylide to oligomerize ethylene.

EXAMPLE I

To 4.01 grams of pyridine (0.05 mole) in 250 milliliters of dichloroethane there was added 6.97 grams of sulfur trioxide (0.087 mole) at 0° C. under nitrogen. After stirring for 0.5 hour, a solution of 19.05 grams of unsubstituted benzoylmethylenetriphenylphosphorane (0.05 mole) in 200 milliliters of dichloroethane was added. This was then heated to reflux for one hour. The reaction mixture was cooled to room temperature and the solvent removed in vacuo. The resulting product was then suspended in ethyl alcohol and filtered to give 19.7 grams of a while solid of the following phosphonium salt in 86 percent yield:

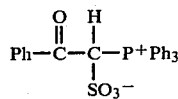

(Compound 1)

Compound 1 was also prepared as follows. To 29 grams of benzoylmethylenetriphenylphosphorane (0.076 mole) in 500 milliliters of dichloroethane at 25° C. under nitrogen there was added 5.47 milliliters of sulfur trioxide (0.132 mole). After stirring for 18 hours the solvent was removed in vacuo. Then 450 milliliters of ethanol and 50 milliliters of water were added and the mixture stirred for one-half hour. The product was filtered and washed with ether to give 31.8 grams, 87 percent yield, of Compound 1.

Compound 1 was then suspended in water and titrated with 10 percent aqueous sodium hydroxide to a phenolphthalein end point. The water was then removed in vacuo and final traces removed via ethanol azeotrope to give 20.7 grams of the following novel ylide in 86 percent yield:

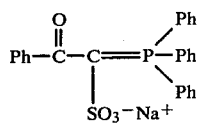

(Compound 2)

When Example I above was repeated except that Compound 1 was titrated with potassium hydroxide and trimethylphenylammonium hydroxide in place of 10 percent aqueous sodium hydroxide the following novel sulfonated ylides, respectively, were obtained:

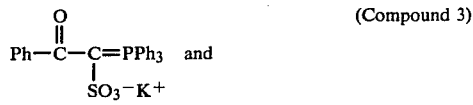

(Compound 3)

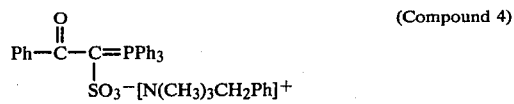

(Compound 4)

EXAMPLE II

The nickel ylide, defined below as Compound 5, was prepared as follows. To 1.38 grams of bis(cyclooctadiene)nickel (five millimoles) in 30 milliliters of tetrahydrofuran there was added a mixture of 1.31 grams of triphenylphosphine (five millimoles) and 2.41 grams of Compound 2 (five millimoles) dissolved in 70 milliliters of tetrahydrofuran. The reaction mixture was stirred for 18 hours at room temperature, after which solvent was removed in vacuo. The resulting solid was dissolved in toluene and filtered. A yellow solid, which precipitated upon addition of heptane, was recovered by filtration. A total yield of 3.65 grams of Compound 5 was recovered in 91 percent yield.

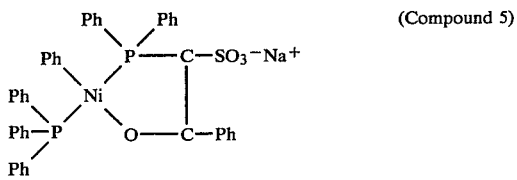

(Compound 5)

EXAMPLE III

A run was carried out wherein there was charged 0.1 millimole of the sulfonated nickel ylide catalyst obtained in Example II, Compound 5, dissolved in 100 milliliters of toluene. During the reaction precautions were taken to exclude air contamination by performing the reaction in an argon atmosphere. The reaction mixture was then heated to 50° C. and pressured with ethylene to obtain a partial pressure thereof of 200 pounds per square inch gauge (1400 kPa). The reaction mixture was stirred throughout the reaction period of two hours, during which time the temperature and pressure were maintained constant. At the end of the two-hour period the reaction mixture was cooled to room temperature and unreacted ethylene removed therefrom by distillation. The amount of oligomer produced was determined and compared with the activity for the compound reported by the Keim et al article previously discussed. The results obtained are set forth in Table II.

TABLE II

| Run No. | Nickel Ylide Catalyst | Activity: Moles Ethylene Converted Per Mole of Nickel Catalyst |
|---|---|---|
| I | Keim et al specific catalyst | 6,000* |
| II | Compound 5 | 20,022 |

*Reported by Keim et al

Compound 5 is more active than the unsulfonated nickel ylide of Keim et al. An additional advantage of Compound 5 over that of Keim et al lies in its easy recovery from the reaction product.

EXAMPLE IV

An additional series of runs were carried out similar to Run No. II but wherein the reactions were carried out at specific elevated temperatures. These data are summarized below in Table III.

TABLE III

| Run No. | Temperature, °C. | Activity: Moles Ethylene Converted Per Mole of Nickel Catalyst |
|---|---|---|
| II | 50 | 20,022 |
| III | 70 | 16,811 |
| IV | 90 | 3,123 |
| V | 120 | 3,814 |
| VI | 150 | 816 |

Although the invention has been described in considerable detail with particular reference to certain preferred embodiments thereof, variations and modifications can be effected within the spirit and scope of the invention as described hereinbefore, and as defined in the appended claims.

We claim:

1. A Group VA ylide defined by the following formula:

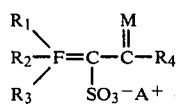

wherein $R_1$, $R_2$, $R_3$, and $R_4$ are either alike or different members selected from the group consisting of hydrogen, alkyl radicals having from about one to about 24 carbon atoms, aryl radicals having from about six to about 20 carbon atoms, alkenyl radicals having from about two to about 30 carbon atoms, cycloalkyl radicals having from about three to about 40 carbon atoms, aralkyl and alkaryl radicals having from about six to about 40 carbon atoms, halogen radicals, hydroxyl, alkoxy, or aryloxy groups, hydrocarbyl groups carrying halogen, hydroxyl, alkoxy or aryloxy, and a sulfonato group or an alkyl, aryl, alkenyl, cycloalkyl, aralkyl or alkaryl group carrying a sulfonato group; M is sulfur or oxygen; F is phosphorus, arsenic or antimony; and A is the cationic residue of a base selected from the group consisting of an alkyl or aryl lithium, an alkoxide and a hydrocarbyl-substituted ammonium hydroxide.

2. An ylide as defined in claim 1 wherein F is phosphorous and M is oxygen.

3. An ylide as defined in claim 1 wherein each of $R_1$, $R_2$, $R_3$ and $R_4$ is phenyl.

4. An ylide as defined in claim 2 wherein each of $R_1$, $R_2$, $R_3$ and $R_4$ is phenyl.

5. An ylide as defined in claim 4 wherein A is potassium.

6. A process for preparing an ylide defined by the following formula:

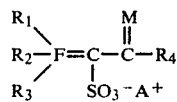

which comprises reacting a sulfonated ylide defined by the following formula:

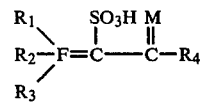

with a base selected from the group consisting of an alkyl or aryl lithium, an alkoxide and a hydrocarbyl-substituted ammonium hydroxide wherein $R_1$, $R_2$, $R_3$ and $R_4$ are either alike or different members selected from the group consisting of hydrogen, alkyl radicals having from about one to about 24 carbon atoms, aryl radicals having from about six to about 20 carbon atoms, alkenyl radicals having from about two to about 30 carbon atoms, cycloalkyl radicals having from about three to about 40 carbon atoms, aralkyl and alkaryl radicals having from about six to about 40 carbon atoms, halogen radicals, hydroxyl, alkoxy, or aryloxy groups, hydrocarbyl groups carrying halogen, hydroxyl, alkoxy or aryloxy, and a sulfonato group or an alkyl, aryl, alkenyl, cycloalkyl, aralkyl or alkaryl group carrying a sulfonato group; M is sulfur or oxygen; F is phosphorus, arsenic or antimony; and A is the cationic portion of the base used.

7. A process as defined in claim 6 wherein F is phosphorus and M is oxygen.

8. A process as defined in claim 6 wherein each of $R_1$, $R_2$ and $R_3$ is phenyl.

9. A process as defined in claim 7 wherein each of $R_1$, $R_2$ and $R_3$ is phenyl.

10. A process as defined in claim 6 wherein said base is trimethylphenylammonium hydroxide.

11. A process as defined in claim 9 wherein said base is trimethylphenylammonium hydroxide.

12. A process as defined in claim 6 wherein said sulfonated ylide is reacted with said base at a temperature of from about room temperature to about 200° C. for about one minute to about four hours.

13. A process as defined in claim 6 wherein said sulfonated ylide is reacted with said base at a temperature of from about room temperature to about 50° C. for about one to about two hours.

14. A process as defined in claim 9 wherein said sulfonated ylide is reacted with said base at a temperature of from about room temperature to about 200° C. for about one minute to about four hours.

15. A process as defined in claim 9 wherein said sulfonated ylide is reacted with said base at a temperature of from about room temperature to about 50° C. for about one to about two hours.

16. A process as defined in claim 10 wherein said sulfonated ylide is reacted with said base at a temperature of from about room temperature to about 200° C. for about one minute to about four hours.

17. A process as defined in claim 10 wherein said sulfonated ylide is reacted with said base at a temperature of from about room temperature to about 50° C. for about one to about two hours.

18. A process as defined in claim 11 wherein said sulfonated ylide is reacted with said base at a temperature of from about room temperature to about 200° C. for about one minute to about four hours.

19. A process as defined in claim 11 wherein said sulfonated ylide is reacted with said base at a temperature of from about room temperature to about 50° C. for about one to about two hours.

20. A process for preparing a sulfonated ylide defined by the following formula:

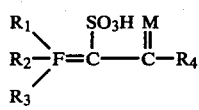

which comprises dissolving the ylide defined by the following formula:

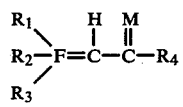

in a solvent and then adding SO₃ to the resulting solution, wherein $R_1$, $R_2$, $R_3$ and $R_4$ are either alike or different members selected from the group consisting of hydrogen, alkyl radicals having from about one to about 24 carbon atoms, aryl radicals having from about six to about 20 carbon atoms, alkenyl radicals having from about two to about 30 carbon atoms, cycloalkyl radicals having from about three to about 40 carbon atoms, aralkyl and alkaryl radicals having from about six to about 40 carbon atoms, halogen radicals, hydroxyl, alkoxy, or aryloxy groups, and hydrocarbyl groups carrying halogen, hydroxyl, alkoxy or aryloxy; M is sulfur or oxygen; and F is phosphorus, arsenic or antimony.

21. A process as defined in claim 20 wherein F is phosphorus and M is oxygen.

22. A process as defined in claim 20 wherein each of $R_1$, $R_2$, $R_3$ and $R_4$ is phenyl.

23. A process as defined in claim 21 wherein each of $R_1$, $R_2$, $R_3$ and $R_4$ is phenyl.

24. A process as defined in claim 22 wherein said sulfonation is carried out at a temperature of about 0° to about 200° C. for about five minutes to about 24 hours.

25. A process as defined in claim 20 wherein said sulfonation is carried out at a temperature of about 20° to about 100° C. for about ten minutes to about four hours.

26. A process as defined in claim 23 wherein said sulfonation is carried out at a temperature of about 0° to about 200° C. for about five minutes to about 24 hours.

27. A process as defined in claim 23 wherein said sulfonation is carried out at a temperature of about 20° to about 100° C. for about ten minutes to about four hours.

28. A Group VA ylide defined by the following formula:

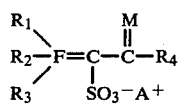

wherein F is phosphorus, M is oxygen, each of $R_1$, $R_2$, $R_3$ and $R_4$ is phenyl and A is trimethylphenylammonium.

29. An ylide as defined in claim 1 wherein A is hydrocarbyl-substituted ammonium hydroxide.

30. An ylide as defined in claim 2 wherein A is hydrocarbyl-substituted ammonium hydroxide.

31. An ylide as defined in claim 3 wherein A is hydrocarbyl-substituted ammonium hydroxide.

32. An ylide as defined in claim 4 wherein A is hydrocarbyl-substituted ammonium hydroxide.

33. An ylide as defined in claim 1 wherein A is trimethylphenylammonium.

34. An ylide as defined in claim 2 wherein A is trimethylphenylammonium.

35. An ylide as defined in claim 3 wherein A is trimethylphenylammonium.

36. A process for preparing an ylide defined by the following formula:

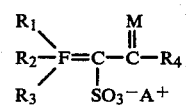

which comprises reacting a sulfonated ylide defined by the following formula:

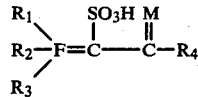

with trimethylphenylammonium hydroxide wherein F is phosphorus, M is oxygen, each of $R_1$, $R_2$ and $R_3$ is phenyl and A is trimethylphenylammonium.

37. A process as defined in claim 36 wherein said sulfonated ylide is reacted with said base at a temperature of from about room temperature to about 200° C. for about one minute to about four hours.

38. A process as defined in claim 36 wherein said sulfonated ylide is reacted with said base at a temperature of from about room temperature to about 50° C. for about one to about two hours.

39. A process as defined in claim 6 wherein said base is a hydrocarbyl-substituted ammonium hydroxide.

40. A process as defined in claim 7 wherein said base is a hydrocarbyl-substituted ammonium hydroxide.

41. A process as defined in claim 8 wherein said base is a hydrocarbyl-substituted ammonium hydroxide.

42. A process as defined in claim 9 wherein said base is a hydrocarbyl-substituted ammonium hydroxide.

43. A process as defined in claim 6 wherein said base is trimethylphenylammonium hydroxide.

44. A process as defined in claim 7 wherein said base is trimethylphenylammonium hydroxide.

45. A process as defined in claim 8 wherein said base is trimethylphenylammonium hydroxide.

46. A process as defined in claim 9 wherein said base is trimethylphenylammonium hydroxide.

* * * * *